United States Patent [19]

Cambon et al.

[11] B 4,000,150
[45] Dec. 28, 1976

[54] PERFLUOROALKYL ISOXAZOLES

[75] Inventors: Aime Cambon; Francois Jeanneaux; Colette Massyn, all of Nice, France

[73] Assignee: Produits Chimiques Ugine Kuhlmann, Paris, France

[22] Filed: May 21, 1974

[21] Appl. No.: 471,836

[44] Published under the second Trial Voluntary Protest Program on February 24, 1976 as document No. B 471,836.

[30] Foreign Application Priority Data

May 22, 1973 France .............................. 73.18486

[52] U.S. Cl. .......................... 260/307 H; 252/78.1; 252/357; 260/307 F
[51] Int. Cl.² ....................................... C07D 261/08
[58] Field of Search ................................ 260/307 H

[56] References Cited
OTHER PUBLICATIONS

Quilico, A. — "Chemistry of Heterocyclic Compounds" vol. 17 (1962) Wiley Press — pp. 6–7, 105.

Primary Examiner—Raymond V. Rush
Attorney, Agent, or Firm—Pennie & Edmonds

[57] ABSTRACT

Perfluoroalkylated isoxazoles having the formula:

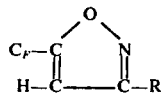

wherein $R_F$ is $C_3 - C_{15}$ perfluoroalkyl and R is the same as $R_F$ or a different $C_3 - C_{15}$ perfluoroalkyl or $C_1 - C_7$ alkyl or phenyl or phenyl substituted by $C_1 - C_7$ alkyl which are prepared by reacting hydroxylamine with a beta-diketone, at least one of whose alkyls is a $C_3 - C_{15}$ perfluoroalkyl, and dehydrating the resultant perfluoroalkylated 5-hydroxy-isoxazoline in an autoclave in the presence of polyphosphoric acid. The stable products are useful as heat-exchange media and as surfactants in organic solution.

1 Claim, No Drawings

PERFLUOROALKYL ISOXAZOLES

BACKGROUND OF THE INVENTION

Substituted isoxazoles are known having the formula

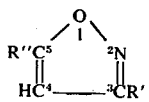

wherein R' and R'' are aliphatic or aromatic hydrocarbon groups. Such isoxazoles are described, for example, in A. QUILICO, "CHEMISTRY OF HETEROCYCLIC COMPOUNDS," Vol. 17, page 1.

Some of the substituted isoxazoles have been synthesized by the reaction of hydroxylamine with a beta-diketone

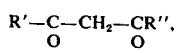

such as by L. CLAISEN, BERICHTE 24 3900 (1891).

Corresponding intermediate 5-hydroxy-isoxazolines have not been synthesized in practice because the reactions leading to them are generally not arrested at that stage but proceed directly to produce the isoxazole, and they can not be isolated.

SUMMARY OF THE INVENTION

The present invention provides new isoxazoles substituted by at least one perfluoroalkyl group. In these new isoxazoles, R' can be and R'' must be a perfluoroalkyl group. The new compounds have unique properties resulting from the highly lyophilic character of the perfluorinated groups and are useful as surface properties, modifiers in organic solution. Their high thermal stability and high rates of transmitting heat make them ideal substances for heat-exchange media.

Briefly stated this invention relates to a perfluoroalkylated isoxazole having the formula:

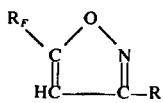

determined by mass spectrum wherein $R_F$ is a $C_3 - C_{15}$ perfluoroalkyl group and R is the same as $R_F$ or a different $C_3 - C_{15}$ perfluoroalkyl group or a $C_1 - C_7$ alkyl group or a phenyl group or a phenyl group substituted by a $C_1 - C_7$ alkyl group.

Present applicants have found that the perfluoroalkylated 5-hydroxy-isoxazolines corresponding to said isoxazoles are surprisingly stable and can be obtained in pure form. The invention therefore relates also to perfluoroalkylated 5-hydroxyisoxazolines having the structure:

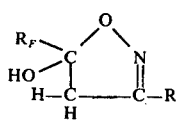

wherein $R_F$ and R have the same meanings as above stated.

This invention relates also to a method of making a perfluorinated 5-hydroxy-isoxazoline which comprises reacting, in a solvent containing at least one $C_1 - C_4$ aliphatic alcohol and in the presence of an acid like hydrochloric, sulfuric or acetic acid, hydroxylamine with a beta-diketone having the formula

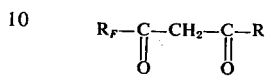

wherein $R_F$ is a $C_3 - C_{15}$ perfluoroalkyl group and R is the same as $R_F$ or a different $C_3 - C_{15}$ perfluoroalkyl group or a $C_1 - C_7$ alkyl group or a phenyl group or a phenyl group substituted by a $C_1 - C_7$ alkyl group. The isoxazolines are a necessary step in the synthese of the isoxazoles. They are synthesis intermediates.

Present applicants have also found that the perfluoroalkylated 5-hydroxy-isoxazolines can be dehydrated only with difficulty. Accordingly, the invention relates also to a method of preparing a perfluoroalkylated isoxazole which comprises dehydrating a perfluoroalkylated 5-hydroxy-isoxazoline in the presence of polyphosphoric acid at a temperature from about 150° to 220°C for at least 24 hours.

This invention also relates to the use of the new substituted isoxazoles and isoxazolines as heat-exchange fluids and as surfactants in organic solutions.

DETAILED DESCRIPTION

The perfluorinated alkyl groups $R_F$ in the 5-position and possibly in the 3-position in the isoxazoles and isoxazolines of this invention can be any straight chain, branched or cyclic alkyl group having from 3 to 15 carbon atoms and having substantially all if its hydrogens replaced by fluorine. Exemplarily, said alkyl group can be heptafluoro-n-propyl, heptafluoroisopropyl, nonafluoro-n-butyl, nonafluoro-isobutyl, nonafluorosecondary butyl, nonafluorotertiary butyl, undecafluoro-n-amyl, undecafluoro-isoamyl, undecafluoro-tertiary amyl, tridecafluoro-n-hexyl, undecafluoro-cyclohexyl, pentadecafluoroheptyl, heptadecafluoro octyl, heptadecafluoro-2-ethylhexyl, nonadecafluorononyl, perfluorodecyl ($C_{10}F_{21}$), perfluoroundecyl ($C_{11}F_{23}$), perfluorolauryl ($C_{12}F_{25}$), perfluoromyristyl ($C_{14}F_{29}$), perfluorotridecyl ($C_{13}F_{27}$), perfluoropentadecyl ($C_{15}F_{31}$), and the like. The preferred perfluoroalkyl groups $R_F$ are heptafluoropropyl, undecafluoroamyl and pentadecafluoroheptyl.

In the isoxazole and isoxazoline products of this invention, one of the groups in the 3 or 5 position must be perfluorinated alkyl as above described. The second substituent R in the 3 or 5 position can likewise be such a perfluorinated alkyl or it can be a $C_1 - C_7$ alkyl, a phenyl or a phenyl substituent in any place on the ring by a $C_1 - C_7$ alkyl. Thus, exemplarily, R can be methyl, ethyl, n-propyl, isopropyl, n-butyl, isobutyl, secondary butyl, tertiary butyl, n-amyl, isoamyl, tertiary amyl, cyclo-pentyl, n-hexyl, cyclohexyl, heptyl and the like; phenyl, or a phenyl substituted in the ortho, meta or para position by a $C_1 - C_7$ alkyl group, thus o-tolyl, p-tolyl, m-tolyl, o-ethyl, phenyl, m-isopropylphenyl, p-propylphenyl, p-butylphenyl, p-amylphenyl, p-hexylphenyl, p-heptylphenyl, and the like. Phenyl, isobutyl and tertiobutyl are preferred.

The preferred method of preparing the isoxazolines of this invention comprises reacting hydroxylamine or an acid salt of hydroxylamine such as hydroxylamine hydrochloride with a beta-diketone which has the desired groups $R_F$ and R; thus, for example,

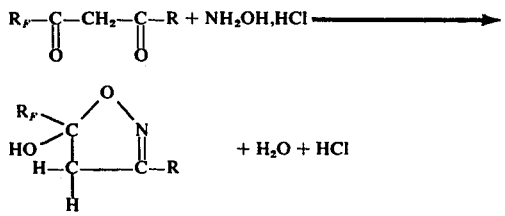

wherein $R_F$ and R have the same meanings as above set forth.

The reaction can conveniently be carried out in a suitable solvent. The preferred solvents are $C_1 - C_4$ aliphatic alcohols, namely methanol, ethanol n-propanol isopropanol, butyl alcohol, tertiary butyl alcohol and the like or in mixtures water-alcohols. In general, ethanol is the preferred solvent.

The reaction can proceed satisfactorily over a wide range of temperature. In general, it is preferred to have the reactants in contact with agitation over a period of about 12 hours or more at ambient temperature, exemplarily at about 10–30°C, preferably at 15°–25°C, followed by a period of about one hour or more at a higher temperature such as between 60° and 120°C. The temperature can be maintained by any of the common procedures. For the second period at elevated temperature it is convenient to heat the solvent to refluxing conditions and to maintain reflux during this final period of the reaction.

It is also helpful to carry out the reaction in the presence of a catalytic amount of a strong acid. Any strong acid is suitable, including exemplarily, hydrochloric acid, sulfuric acid, phosphoric acid, toluene sulfuric acid and the like. Hydrochloric acid is preferred. Exemplarily, the use of acid in amount corresponding to a concentration of 0.1 to 0.5 equivalents of hydrogen ion per liter of reaction medium affects a rate of reaction capable of obtaining good yields with the stated duration and temperatures of reaction. When hydroxylamine is added as an acid salt, the acidity of the acid can contribute to the catalytic activity.

In contacting the reactants, either the hydroxylamine or the diketone can be used in excess over the stoichiometric amount. Thus exemplarily from about 0.7 to 3 mols of hydroxylamine hydrochloride can be used with one mole of diketone. Either reactant can be added gradually to the other, or the reactants can be simply mixed and allowed to react.

After the finishing off at the higher temperature, the reaction mixture can then be poured into ice-water to form a precipitate comprising the desired isoxazoline, which is then recovered by filtration and recrystallized in conventional manner, for example from benzene. The recrystallized product is usually a white crystalline powder.

The beta-diketones which are used in carrying out this invention can be prepared by perfluoroacylation of appropriate ketones by esters or acid chlorides of perfluorocarboxylic acids, as in the reaction of methyl perfluorocaprylate with methyl tertiary butyl ketone to make 1-perfluoroheptyl-3 tertiary butyl-1,3 propanedione. Or a methyl perfluoroalkyl ketone can be acylated by an appropriate carboxylic derivative, as in the reaction of methyl phenylacetate with methyl perfluoropentyl ketone to give 1-perfluoropentyl-3-phenyl-1,3-propanedione; or in order to have two perfluorinated groups in the eventual isoxazoline, a methyl ketone containing also a perfluoroalkyl group can be acylated by an ester of a perfluorinated carboxylic acid, as when methyl perfluorocaprylate is reacted with methyl perfluoroheptyl ketone to produce 1,3-di(perfluoroheptyl)-1,3-propanedione.

Among the beta-diketones which can be used in the present invention, some having polyfluorinated lower alkyl groups are known and disclosed, for example, in R. A. MOORE and R. LEVINE J. ORG. CHEM. 29 page 1439 (1964). Others have been synthesized for the first time by present inventors.

The perfluoroalkylated isoxazoles of this invention are prepared from the described perfluoroalkylated hydroxy-isoxazolines by dehydration. The removal of water from the perfluoroalkylated hydroxy-isoxazolines is surprisingly difficult. Accordingly, the present Applicants prefer to heat in a closed vessel for at least 24 hours at a temperature in the range of 150°–220°C. in the presence of a dehydrating amount of polyphosphoric acid, exemplarily an amount of polyphosphoric acid corresponding to between 10 and 20 times the weight of the perfluoroalkylated isoxazoline. Sulfuric acid and phosphor pentoxide can also be employed as dehydrating agent.

By polyphosphoric acid, there is designated the mixture obtained by heating $H_3PO_4$ with sufficient phosphoric anhydride to provide a $P_2O_5$ content in the range of about 82–85 %.

After the dehydration step, the reaction product comprising the desired perfluoroalkylated isoxazole is conveniently precipitated by pouring into water with agitation. The resulting precipitate can be filtered and washed in conventional manner, for example, successively by water and by aqueous sodium carbonate solution. Purification can exemplarily be by passage over a column of suitable adsorbent such as alumina and eluting with a suitable solvent such as ethyl ether. The desired isoxazole is usually obtained in the form of well-crystallized long needles.

When the objective is to obtain a perfluoroalkylated isoxazole, starting from the appropriate diketone, it is not required to obtain a pure crystalline isoxazoline intermediate. The product of condensing the diketone and hydroxylamine can be separated in crude form, either as a precipitate on addition to cold water or as a residue from the evaporation of the reaction mixture, and placed after drying directly in polyphosphoric acid for the dehydration step.

The new isoxazoles of this invention have numerous applications, chiefly as heat-exchange fluids and as surface active agents in organic solution.

The invention will be further illustrated by description in connection with the following specific examples of the practice of it, the proportions here and elsewhere herein being expressed in parts by weight unless specifically stated to the contrary.

EXAMPLE 1

A 0.01 mol quantity (5.16 grams of 1-n-pentadecafluoroheptyl-1-phenyl-1,3 propanedione, dispersed in 20 cc. of 0.5 normal hydrochloric acid, was added to 20 cc. of ethylalcohol which was just about sufficient to dissolve the diketone. There was then added 0.02 mol (1.4 grams) of hydroxylamine hydrochloride dissolved in 5 cc. of water. The solution was kept under agitation, at ambient temperature about 20°C, for twelve hours and then heated under reflux for one hour. The reaction mixture was poured into 100 cc. of ice-water and the 5-hydroxy-2-isoxazoline which precipitated in the form of a white powder, was recovered by filtration and recrystallized three times from benzene. There was obtained 4.9 grams of 5-n-pentadecafluoroheptyl-3-phenyl-5-hydroxy-isoxazoline, corresponding to a yield of 92 % based on the starting diketone. The product had a melting point of 145°C. Spectra and the following analysis results correspond to the stated structure.

|  | Calculated from $C_{16}H_8F_{15}NO_2$ | Found |
| --- | --- | --- |
| % Carbon | 36.16 | 36.16 |
| % Hydrogen | 1.50 | 1.37 |
| % Nitrogen | 2.63 | 2.70 |
| % Fluorine | 53.67 | 53.34 |

EXAMPLE 2

Using a procedure similar to that described in Example 1, hydroxylamine hydrochloride was reacted with 1-n-undecafluoroamyl-3-phenyl-1,3 propanedione. A product corresponding to the structure 5-n-undecafluoroamyl-3-phenyl-5-hydroxy-isoxazoline was obtained, having a melting point at 139°C. The yield was 90 % of theoretical.

EXAMPLE 3

Using a procedure similar to that described in Example 1, hydroxylamine hydrochloride was reacted with 1-n-heptafluoropropyl-3-phenyl-1,3-propanedione. A product corresponding to the structure 5-n-heptafluoropropyl-3-phenyl-5-hydroxy-isoxazoline was obtained, melting at 120°C. The yield was 92 % of theoretical.

EXAMPLE 4

Using the Example 1 procedure, hydroxylamine hydrochloride was reacted with 1-n-perfluoroheptyl-3-tertiary butylpropanedione. A product corresponding to the structure 5-n-perfluoroheptyl-3-tertiary butyl-5-hydroxy isoxazoline was obtained, melting at 92°C. The yield was 94 % of theoretical.

EXAMPLE 5

Using the Example 1 procedure, hydroxylamine hydrochloride was reacted with 1,3-di(n-perfluoroheptyl)-1,3-propanedione. A product corresponding to the structure 3,5-di-n-perfluoroheptyl-5-hydroxy-isoxazoline was obtained, melting at 106°C. The yield was 83 % of theoretical.

EXAMPLE 6

A 0.005 mol quantity (2.7 grams) of the 5-n-pentadecafluoroheptyl-3-phenyl-5-hydroxy-isoxazoline prepared in Example 1 was placed in a glass tube together with 40 grams of polyphosphoric acid and sealed. The sealed tube was maintained in an autoclave for 24 hours at 180°–200°C. The tube was then cooled to room temperature, and opened, and the contents were poured into 250 cc. of water, which was stirred vigorously for 15 minutes. The grey precipitate was filtered off and washed successively with water and with 10 % aqueous sodium carbonate solution. The solution was purified by passing it through a column of alumina and eluting with ether. The ether was allowed to evaporate from the eluent at ambient temperature. There was obtained 2.3 grams of 5-n-pentadecafluoroheptyl-3-phenyl-isoxazole in the form of long colorless needles. The yield was 88 % based on the weight of the isoxazoline and 81 % based on the starting diketone. The isoxazole melted at 87°C. Its infrared spectrum, nuclear magnetic resonance spectrum, mass spectrum and ultra-violet spectrum are all in accord with the stated structure, as are also the analytical results presented below. Attention is called to the fact that the isomer obtained has the perfluorinated alkyl in the 5-position; i.e., on the carbon next to the oxygen in the ring.

| Analytical Data | | |
| --- | --- | --- |
|  | Calculated from $C_{16}H_6F_{15}NO$ | Found |
| % Carbon | 37.42 | 37.49 |
| % Hydrogen | 1.17 | 1.21 |
| % Nitrogen | 2.74 | 2.68 |
| % Fluorine | 55.55 | 55.53 |

EXAMPLE 7

Using a procedure similar to that described in Example 6, a portion of the 5-n-undecafluoroamyl-3-phenyl-5-hydroxyisoxazoline obtained in Example 2 was dehydrated, yielding a product which was entirely the isomer 5-n-undecafluoroamyl-3-phenylisoxazole, melting at 58°C. The yield was 90 % based on the weight of the isoxazoline, 81 % based on the starting beta-diketone in Example 2.

EXAMPLE 8

Using a procedure similar to that described in Example 6, a portion of the 5-n-heptafluoropropyl-3-phenyl-5-hydroxy-isoxazoline obtained in Example 3 was dehydrated, yielding a product which was entirely the isomer 5-n-heptafluoropropyl-3-phenyl isoxazole, melting at 34°C. The yield was 89 % based on the weight of the isoxazoline, 82 % based on the starting beta-diketone in Example 3.

EXAMPLE 9

Using a procedure similar to that described in Example 6, a portion of the 5-n-perfluoroheptyl-3-tertiarybutyl-5-hydroxyisoxazoline obtained in Example 4 was dehydrated, yielding a product which was entirely the isomer 5-n-perfluoro-heptyl-3-tertiarybutyl isoxazole, melting at 45°C. The yield was 85 % based on the weight of the isoxazoline, 80 % based on the starting beta-diketone in Example 4.

EXAMPLE 10

Using a procedure similar to that described in Example 6, a portion of the 3,5-di-n-perfluoroheptyl-5-hydroxy-isoxazoline obtained in Example 5 was dehydrated, yielding a product which was 3,5-di-n-perfluoroheptyl isoxazole, melting at 52°C. The yield was 75 % based on the weight of the isoxazoline, 64 % based on the starting beta-diketone in Example 5.

We claim:

1. A perfluoroalkylated isoxazole having the formula:
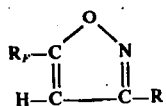
wherein $R_F$ is $C_3$–$C_{15}$ perfluoroalkyl and R is the same as $R_F$ or a different $C_3$–$C_{15}$ perfluoroalkyl or $C_1$–$C_7$ alkyl or phenyl or phenyl substituted by a $C_1$–$C_7$ alkyl.
* * * * *